United States Patent
Nakamura et al.

(10) Patent No.: US 10,011,553 B2
(45) Date of Patent: Jul. 3, 2018

(54) METHOD FOR PRODUCING DRY ETCHING GAS

(71) Applicant: DAIKIN INDUSTRIES, LTD., Osaka (JP)

(72) Inventors: Shingo Nakamura, Osaka (JP); Yuusuke Etou, Osaka (JP); Tatsuya Ohtsuka, Osaka (JP); Kanako Fukumoto, Osaka (JP); Masato Naitou, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/436,248

(22) PCT Filed: Nov. 12, 2013

(86) PCT No.: PCT/JP2013/080563
§ 371 (c)(1),
(2) Date: Apr. 16, 2015

(87) PCT Pub. No.: WO2014/077246
PCT Pub. Date: May 22, 2014

(65) Prior Publication Data
US 2015/0299088 A1 Oct. 22, 2015

(30) Foreign Application Priority Data

Nov. 14, 2012 (JP) ................. 2012-250311

(51) Int. Cl.
| | | |
|---|---|---|
| *C07C 51/58* | (2006.01) | |
| *C07C 17/361* | (2006.01) | |
| *C07C 17/383* | (2006.01) | |
| *C07C 51/64* | (2006.01) | |
| *C07C 17/38* | (2006.01) | |
| *C07C 41/06* | (2006.01) | |

(52) U.S. Cl.
CPC ............ *C07C 51/58* (2013.01); *C07C 17/361* (2013.01); *C07C 17/38* (2013.01); *C07C 17/383* (2013.01); *C07C 41/06* (2013.01); *C07C 51/64* (2013.01)

(58) Field of Classification Search
None
See application file for complete search history.

(56) References Cited

U.S. PATENT DOCUMENTS

| 4,357,282 A | 11/1982 | Anderson et al. |
|---|---|---|
| 5,710,317 A | 1/1998 | Oharu et al. |
| 2013/0012740 A1 | 1/2013 | Okamoto et al. |

FOREIGN PATENT DOCUMENTS

| JP | 56-40617 | 4/1981 |
|---|---|---|
| JP | 61-45972 | 10/1986 |
| JP | 4-7330 | 1/1992 |
| JP | 8-92162 | 4/1996 |
| JP | 2006-111611 | 4/2006 |
| JP | 2012-180285 | * 9/2012 |
| WO | 2011/102268 | 8/2011 |

OTHER PUBLICATIONS

Machine translation of JP 2012-180285.*
International Search Report dated Jan. 28, 2014 in International (PCT) Application No. PCT/JP2013/080563.
England, "Catalytic Conversion of Fluoroalkyl Alkyl Ethers to Carbonyl Compounds", J. Org. Chem., vol. 49, No. 21, 1984, pp. 4007-4008.
Inouye et al.,"2-Hydryl-2-(F-Methyl)-F-Propanoyl Fluoride as a Useful Building Block for the Synthesis of Trifluoromethylated Heterocyclic Compounds, Synthesis of 1,3-Dimethyl-2,3-Dihydro-5-(F-Methyl)-6-Fluoro-2-Thioxo-4(1H)-Pyrimidinone and 1,3-Dimethyl-5-(F-Methyl)-6-Fluoro-2,4(1H,3H)-Pyrimidinedione", Journal of Fluorine Chemistry, vol. 27, 1985, pp. 379-384.

* cited by examiner

*Primary Examiner* — Sudhakar Katakam
*Assistant Examiner* — Ana Z Muresan
(74) *Attorney, Agent, or Firm* — Wenderoth, Lind & Ponack, L.L.P.

(57) ABSTRACT

Provided is a method for producing fluoromethane and 3,3,3-trifluoro-2-(trifluoromethyl)propanoyl fluoride (($CF_3$)$_2$CHCOF), which are useful as dry etching gases etc., safely and inexpensively with high purity.
According to the method in which 1,1,3,3,3-pentafluoro-2-trifluoromethylpropyl methyl ether is pyrolyzed in a gas phase in the presence of a catalyst, the desired fluoromethane and 3,3,3-trifluoro-2-(trifluoromethyl)propanoyl fluoride can be obtained with high selectivity and high conversion of the starting material by a simple process in which a pyrolysis reaction is performed in a gas phase using the inexpensive starting material.

11 Claims, No Drawings

METHOD FOR PRODUCING DRY ETCHING GAS

TECHNICAL FIELD

The present invention relates to a method for simultaneously producing fluoromethane and 3,3,3-trifluoro-2-(trifluoromethyl)propanoyl fluoride, which are useful as dry etching gases.

BACKGROUND ART

Hydrofluorocarbons are useful as etching gases for the microfabrication of semiconductors, liquid crystals, and the like. In particular, fluoromethane ($CH_3F$) is drawing attention as an etching gas for forming state-of-the-art microstructures.

Known methods for producing fluoromethane are, for example, as follows:
(1) a method in which methyl alcohol and hydrogen fluoride are reacted using a catalyst (Patent Literature 1);
(2) a method in which methyl chloride and hydrogen fluoride are reacted using a catalyst (Patent Literature 2); and
(3) a method in which 1-methoxy-1,1,2,2-tetrafluoroethane is pyrolyzed (Patent Literature 3).

Among these methods, method (1) has drawbacks in that the catalyst tends to deteriorate because a large amount of water is produced, and corrosion tends to occur because hydrofluoric acid is produced from the unreacted hydrogen fluoride and the produced water. In method (2), it is necessary to add excess hydrogen fluoride to improve reactivity in fluorination. Recycling and reusing such hydrogen fluoride necessitates larger equipment, and thus the cost of production equipment becomes excessive. Further, there are problems with respect to decreased reactivity and corrosion due to moisture contamination or the like.

Method (3) requires energy for cooling to separate fluoromethane (boiling point of −79° C.) from difluoroacetyl fluoride simultaneously produced with fluoromethane, because difluoroacetyl fluoride has a low boiling point of 0° C. In addition, many impurities with low boiling points are contained, and separation of the impurities from fluoromethane is difficult even if rectification is performed. Among the impurities, in particular, trifluoromethane ($CHF_3$), which has a boiling point of −84° C., is difficult to separate since the boiling point is close to that of fluoromethane. Besides, since the conversion of the starting material is associated with the amount of trifluoromethane produced, it may be necessary to decrease the conversion in the reaction to reduce the amount of trifluoromethane, thus posing the problem of a decrease in the production efficiency of fluoromethane. Furthermore, 1-methoxy-1,1,2,2-tetrafluoroethane used as a starting material is synthesized by reacting tetrafluoroethylene and methanol, and thus the method involves the risk of handling tetrafluoroethylene and causes a problem in that the costs of the starting material and equipment become expensive.

Meanwhile, cleaning gases, such as $C_2F_6$ and $NF_3$, and etching gases, such as $SF_6$, are dry process gases used in large quantities in production processes for semiconductors and liquid crystals. However, because these gases have large global warming effects, there is a demand for alternative gases. 3,3,3-trifluoro-2-(trifluoromethyl)propanoyl fluoride is expected to serve as such an alternative gas.

Patent Literature 4 listed below discloses that 3,3,3-trifluoro-2-(trifluoromethyl)propanoyl fluoride was obtained in a yield of 85% by cooling 1,1,3,3,3-pentafluoro-2-trifluoromethylpropyl methyl ether to −40° C. to liquefy the ether, adding $SbF_5$, and allowing a reaction to proceed at not greater than room temperature. However, this method is problematic in that the reaction is performed in a liquid phase using $SbF_5$, which is expensive and corrodes metallic reaction kettles. Further, since the reaction is a batch reaction, the production efficiency is inferior to that of a continuous reaction in a gas phase. Thus, the method is unsuitable for industrial mass production. Patent Literature 4 also discloses that fluoromethane is simultaneously produced with 3,3,3-trifluoro-2-(trifluoromethyl)propanoyl fluoride by this method; however, Patent Literature 4 does not specifically disclose the production amount thereof, and the theoretical yield of fluoromethane is only 85% at most. Therefore, taken together with the above description that the yield of 3,3,3-trifluoro-2-(trifluoromethyl)propanoyl fluoride was 85%, the yield of 3,3,3-trifluoro-2-(trifluoromethyl)propanoyl fluoride and the yield of fluoromethane are both low. Accordingly, higher yields are desired.

Non-patent Literature 1 listed below discloses a method for producing 3,3,3-trifluoro-2-(trifluoromethyl)propanoyl fluoride, wherein 1,1,3,3,3-pentafluoro-2-trifluoromethylpropyl methyl ether is reacted with trimethylamine, followed by a reaction with hydrogen chloride. However, this method is inappropriate as an industrial production method, because the yield is only 46% and both alkali and acid are used in the reaction, thus making the reaction complex and requiring equipment with anticorrosion properties.

CITATION LIST

Patent Literature

PTL 1: JPH04-007330B
PTL 2: JP2006-111611A
PTL 3: WO2011/102268A1
PTL 4: JPS61-045972B

Non-Patent Literature

NPL 1: J. Fluorine Chemistry, 1985, 27(4), pp. 379-384

SUMMARY OF INVENTION

Technical Problem

The present invention has been accomplished in view of the foregoing state of the art, and its primary object is to provide a method for producing fluoromethane and 3,3,3-trifluoro-2-(trifluoromethyl)propanoyl fluoride (($CF_3$)$_2$CHCOF), which are useful as dry etching gases etc., safely and inexpensively with high purity, the method being suitable for industrial production.

Solution to Problem

The present inventors conducted extensive research to achieve the above object. As a result, the inventors found that fluoromethane and 3,3,3-trifluoro-2-(trifluoromethyl) propanoyl fluoride can be obtained in high yields with almost no by-products that make a separation operation complicated, by a simple process in which 1,1,3,3,3-pentafluoro-2-trifluoromethylpropyl methyl ether is used as a starting material, and the starting material is pyrolyzed in a gas phase in the presence of a catalyst. Further, the inventors found that 1,1,3,3,3-pentafluoro-2-trifluoromethylpropyl methyl ether used as a starting material can be obtained by reacting methanol and perfluoroisobutylene, which is a waste material produced in a process for producing fluororesin, and that fluoromethane and 3,3,3-trifluoro-2-(trifluoromethyl)propanoyl fluoride can be efficiently produced using the inexpensive starting material. The present inventors conducted further research based on these findings, thus accomplishing the present invention.

More specifically, the present invention provides the following method for producing fluoromethane and 3,3,3-trifluoro-2-(trifluoromethyl)propanoyl fluoride.

Item 1. A method for producing fluoromethane and 3,3,3-trifluoro-2-(trifluoromethyl)propanoyl fluoride, the method comprising pyrolyzing 1,1,3,3,3-pentafluoro-2-trifluoromethylpropyl methyl ether in a gas phase in the presence of a catalyst.

Item 2. The method according to Item 1, wherein the 1,1,3,3,3-pentafluoro-2-trifluoromethylpropyl methyl ether used as a starting material is obtained by reacting perfluoroisobutylene and methanol.

Item 3. The method according to Item 1, comprising the steps of:
(1) reacting perfluoroisobutylene and methanol to obtain 1,1,3,3,3-pentafluoro-2-trifluoromethylpropyl methyl ether; and
(2) pyrolyzing the 1,1,3,3,3-pentafluoro-2-trifluoromethylpropyl methyl ether obtained in step (1) in a gas phase in the presence of a catalyst to obtain fluoromethane and 3,3,3-trifluoro-2-(trifluoromethyl)propanoyl fluoride.

Item 4. The method according to any one of Items 1 to 3, wherein the catalyst is at least one member selected from the group consisting of metal oxides, fluorinated metal oxides, and metal fluorides.

Item 5. The method according to Item 4, wherein the catalyst is at least one member selected from the group consisting of alumina, chromium oxide, titanium oxide, zinc oxide, fluorinated alumina, fluorinated chromium oxide, fluorinated titanium oxide, fluorinated zinc oxide, $AlF_3$, $TiF_4$, $CrF_3$ and $ZnF_2$.

Item 6. The method according to Item 4, wherein the catalyst is alumina.

Item 7. The method according to Item 5 or 6, wherein the alumina is γ-alumina.

Item 8. The method according to any one of Items 4 to 7, wherein the catalyst has a pore volume of 0.5 ml/g or more.

Item 9. The method according to any one of Items 1 to 8, wherein the temperature of the pyrolysis reaction is in the range of 100 to 400° C.

Item 10. The method according to any one of Items 1 to 9, wherein the pressure during the pyrolysis reaction is in the range of 0.05 to 1 MPa.

Item 11. The method according to any one of Items 1 to 10, further comprising, after obtaining the pyrolyzed product comprising fluoromethane and 3,3,3-trifluoro-2-(trifluoromethyl)propanoyl fluoride, the step of cooling the product to separate it into a low-boiling-point component comprising the fluoromethane and a high-boiling-point component comprising the 3,3,3-trifluoro-2-(trifluoromethyl)propanoyl fluoride.

Item 12. The method according to any one of Items 1 to 10, further comprising, after obtaining the pyrolyzed product comprising fluoromethane and 3,3,3-trifluoro-2-(trifluoromethyl)propanoyl fluoride, the step of bringing the product into contact with water or an aqueous alkaline solution to remove the 3,3,3-trifluoro-2-(trifluoromethyl)propanoyl fluoride.

Item 13. The method according to any one of Items 1 to 10, further comprising, after obtaining the pyrolyzed product comprising fluoromethane and 3,3,3-trifluoro-2-(trifluoromethyl)propanoyl fluoride, the step of subjecting the product to a distillation operation to obtain the 3,3,3-trifluoro-2-(trifluoromethyl)propanoyl fluoride as a column bottom component.

Item 14. The method according to any one of Items 1 to 10, further comprising, after obtaining the pyrolyzed product comprising fluoromethane and 3,3,3-trifluoro-2-(trifluoromethyl)propanoyl fluoride, the step of bringing the product into contact with an alcohol to remove the 3,3,3-trifluoro-2-(trifluoromethyl)propanoyl fluoride.

Item 15. The method according to Item 14, wherein the alcohol is at least one member selected from the group consisting of methanol, ethanol, and propanol.

The production method of the present invention is a method in which 1,1,3,3,3-pentafluoro-2-trifluoromethylpropyl methyl ether is used as a starting material, and a pyrolysis reaction is performed in a gas phase in the presence of a catalyst. Hereinafter, the production method of the present invention is described in more detail.

Starting Compound

In the present invention, 1,1,3,3,3-pentafluoro-2-trifluoromethylpropyl methyl ether represented by the formula: $(CF_3)_2CHCF_2OCH_3$ is used as a starting material. There is no particular limitation on the method for producing 1,1,3,3,3-pentafluoro-2-trifluoromethylpropyl methyl ether used as a starting material, and 1,1,3,3,3-pentafluoro-2-trifluoromethylpropyl methyl ether obtained by any method may be used.

In particular, perfluoroisobutylene ($(CF_3)_2C=CF_2$)), which is obtained as a by-product when octafluorocyclobutane used as a starting material of fluororesin is produced, has hitherto been discarded as waste; however, 1,1,3,3,3-pentafluoro-2-trifluoromethylpropyl methyl ether can be obtained by reacting perfluoroisobutylene with methanol. Use of the thus-obtained 1,1,3,3,3-pentafluoro-2-trifluoromethylpropyl methyl ether as a starting material in the present invention allows for effective utilization of waste and enables the desired product to be produced inexpensively by using the low-cost starting material. In the present invention, the phrase stating that 1,1,3,3,3-pentafluoro-2-trifluoromethylpropyl methyl ether used as a starting material is "obtained by reacting perfluoroisobutylene and methanol" is limited to the meaning that the 1,1,3,3,3-pentafluoro-2-trifluoromethylpropyl methyl ether is obtained by said reaction, and is not obtained by other methods. The method for obtaining 1,1,3,3,3-pentafluoro-2-trifluoromethylpropyl methyl ether by reacting perfluoroisobutylene and methanol is a known method and may be conducted in accordance with known reaction conditions. For example, the reaction may be performed in accordance with the method disclosed in JP2001-506261A.

Pyrolysis Reaction Method

The production method of the present invention is a method in which the above-mentioned 1,1,3,3,3-pentafluoro-2-trifluoromethylpropyl methyl ether is used as a starting material, and a pyrolysis reaction is performed in a gas phase in the presence of a catalyst.

(1) Catalyst

The catalyst is not particularly limited as long as it is active for a pyrolysis reaction in a gas phase. Examples of such catalysts include metal oxides, fluorinated metal oxides, metal fluorides, and the like. These may be used singly or in a combination of two or more.

Of these, preferable examples of metal oxides include alumina, chromium oxide, titanium oxide, zinc oxide, and the like. In addition, fluorinated metal oxides obtained by fluorinating part of these metal oxides may be used. The fluorinated metal oxide catalysts may be those obtained by fluorinating a metal oxide catalyst with hydrogen fluoride or the like beforehand, or metal oxide catalysts that are partly fluorinated in the reaction process of the production method of the present invention. Preferable examples of metal fluorides include $AlF_3$, $TiF_4$, $CrF_3$, $ZnF_2$, and the like.

Among metal oxides, alumina is preferable, and α-alumina, activated alumina, etc., may be used. Examples of usable activated alumina include ρ-alumina, χ-alumina, κ-alumina, η-alumina, pseudo-γ-alumina, γ-alumina, δ-alumina, θ-alumina, and the like. Of these, γ-alumina and η-alumina are preferable, and γ-alumina is particularly preferable. Silica alumina ($SiO_2/Al_2O_3$), a composite oxide, may also be used as a catalyst. The proportion of silica $SiO_2$ in silica alumina is preferably 20 to 90 wt %, and more preferably 50 to 80 wt %.

The larger the pore volume of the catalyst, the higher the activity. The pore volume of the catalyst is preferably 0.4 ml/g or more, and particularly preferably 0.5 ml/g or more. The upper limit of the pore volume of the catalyst is not particularly limited, and is typically 5 ml/g or less, and, in terms of reaction rate and catalyst strength, preferably 2 ml/g or less. The pore volume can be measured by a gas adsorption method, a mercury intrusion method, or the like.

The catalyst may have deposited thereon an alkali metal or alkaline earth metal fluoride, such as KF, NaF, and $MgF_2$.

There is no particular limitation on the method for obtaining the above-mentioned fluorinated metal oxides. For example, the fluorinated metal oxides can be obtained by bringing the above-described metal oxides into contact with anhydrous hydrogen fluoride or a flon (particular halocarbon compounds, such as a chlorofluorocarbon (CFC), a fluorocarbon (FC), a hydrochlorofluorocarbon (HCFC) and a hydrofluorocarbon (HFC), etc.) while heating to allow a fluorination reaction to proceed. The method for bringing the metal oxides into contact with hydrogen fluoride is not particularly limited and may be a continuous flow method in which hydrogen fluoride is allowed to flow through a reaction tube containing the catalyst or a batch method in which hydrogen fluoride or a flon is enclosed in a container containing the catalyst. In particular, the flow method is preferable in terms of a short treatment time.

The flon is preferably one with a large number of fluorine atoms and a small number of carbon atoms. Examples of flon include trifluoromethane, difluorochloromethane, octafluoroethane, and the like.

The degree of fluorination of such a metal oxide is not particularly limited; those having a fluorine content of about 5 to about 50 wt % based on the total weight of fluorinated metal oxide are preferably used.

The temperature of the fluorination treatment for such a metal oxide is preferably higher than that of the below-described pyrolysis reaction and is, for example, preferably about 150° C. to about 500° C., more preferably about 200° C. to about 400° C., and even more preferably about 250° C. to about 350° C. An excessively low temperature in the fluorination treatment decreases the effect of the catalyst because of insufficient fluorination, whereas an excessively high temperature in the fluorination treatment additionally requires a heat-resistant material. Thus, an excessively low temperature or an excessively high temperature is not practical.

(2) Pyrolysis Reaction Conditions

There is no particular limitation on the specific method for allowing a pyrolysis reaction of 1,1,3,3,3-pentafluoro-2-trifluoromethylpropyl methyl ether to proceed by bringing the 1,1,3,3,3-pentafluoro-2-trifluoromethylpropyl methyl ether into contact with the above-described catalyst in a gas phase in the presence of the catalyst. An example is a method in which the catalyst is placed in a tubular flow reactor, and 1,1,3,3,3-pentafluoro-2-trifluoromethylpropyl methyl ether used as a starting material is introduced to the reactor and brought into contact with the catalyst in a gas phase.

If the temperature of the pyrolysis reaction is excessively low, the conversion of the starting material tends to decrease. If the temperature of the pyrolysis reaction is excessively high, impurities tend to increase. Thus, the temperature of the pyrolysis reaction is preferably about 100° C. to about 400° C., more preferably about 100° C. to about 300° C., and particularly preferably about 100° C. to about 250° C.

An excessively low pressure in the reactor during the pyrolysis reaction complicates the operation because of the possible contamination of air, etc., whereas an excessively high pressure in the reactor during the pyrolysis reaction requires that the pressure resistance of the equipment be considered and increases the possibility of leakage. Considering these points, the pressure in the reactor during the pyrolysis reaction is preferably about 0.05 to about 1 MPa, more preferably about 0.1 to about 0.5 MPa, and particularly preferably, in terms of reaction operation, about atmospheric pressure (about 0.1 MPa).

There is no particular limitation on the contact time for the reaction, represented by W/F (g·sec/cc), i.e., the ratio of the amount of the catalyst W (g) relative to the flow rate F (the flow rate at 0° C. and 1 atm (about 0.1 MPa): cc/sec) of the starting material gas, i.e., 1,1,3,3,3-pentafluoro-2-trifluoromethylpropyl methyl ether that is supplied to the reactor. The contact time is preferably about 1 to about 100 g·sec/cc, more preferably about 1 to about 50 g·sec/cc, and even more preferably about 5 to about 30 g·sec/cc. If the contact time is too long, it takes a long time to obtain the product. To increase the amount of production, it is preferred that the contact time be shortened; however, if the contact time is too short, the conversion tends to decrease. Thus, the contact time may be selected so that the highest productivity is obtained in terms of the conversion of the starting material and the selectivity of the desired product, according to the type of catalyst to be used, the amount of the catalyst, the reaction conditions, and the like. In general, it is desirable to conduct the reaction by selecting the contact time so that the conversion becomes 100%, according to the type of catalyst to be used, the amount of the catalyst, the reaction conditions, and the like.

(3) Catalyst Regeneration Treatment

In the method of the present invention, the catalytic activity may decrease with the lapse of the reaction time. In such cases, there is a possibility that the organic substance used as a starting material has been carbonized on the catalyst surface. When the catalytic activity decreases, the catalyst can be regenerated by allowing oxygen-containing gas to flow through the reactor with the catalyst being heated, reacting the carbon adhered to the catalyst surface with the oxygen to form gases such as carbon dioxide and carbon monoxide, and removing them. The temperature in the reactor during catalyst regeneration is preferably about 200° C. to about 500° C., and more preferably about 300° C. to about 400° C. It is efficient to use gas with high purity as the oxygen-containing gas; however, it is economically preferable to use air since a similar effect can be obtained if gas contains oxygen.

The time for catalyst regeneration varies depending on the type of catalyst and the time of use. The time for catalyst regeneration may be any time that can restore sufficient catalytic activity, and may be typically about 1 to about 12 hours.

Product

A pyrolysis reaction of 1,1,3,3,3-pentafluoro-2-trifluoromethylpropyl methyl ether is caused to occur by the above-described method to obtain the desired fluoromethane and 3,3,3-trifluoro-2-(trifluoromethyl)propanoyl fluoride with high selectivity and high conversion of the starting material.

There is no particular limitation on the method for separating the fluoromethane and 3,3,3-trifluoro-2-(trifluoromethyl)propanoyl fluoride contained in the thus-obtained product. For example, the produced gas after the pyrolysis reaction may be cooled to separate it into a gas component comprising a low-boiling-point component that contains the fluoromethane (boiling point of −79° C.) as a main component, and a liquid component comprising a high-boiling-point component that contains the 3,3,3-trifluoro-2-(trifluoromethyl)propanoyl fluoride (boiling point of 32° C.) as a main component and further may contain the unreacted starting material 1,1,3,3,3-pentafluoro-2-trifluoromethylpropyl methyl ether (boiling point of 68.5° C.). In this case, the cooling temperature is not particularly limited. The produced gas may be cooled to a temperature of, for example, about −4 to about 30° C.

By the above method, the component containing the fluoromethane can be separated as a gas component. The gas component may contain propene (boiling point of −47.7° C.), pentafluoropropene (boiling point of −21.1° C.), propane (boiling point of −1.4° C.), etc., as impurities. However, these impurities can be easily separated by distillation since fluoromethane and these impurities have very different boiling points.

In addition, when the high-boiling-point component, which is obtained as a liquid component and contains the 3,3,3-trifluoro-2-(trifluoromethyl)propanoyl fluoride (boiling point of 32° C.) as a main component, contains the unreacted starting material, etc., the unreacted starting material, etc., can be easily separated by distillation.

With respect to the method for selectively obtaining fluoromethane, the product obtained after the pyrolysis reaction may be brought into contact with water, an aqueous alkaline solution, or the like to dissolve 3,3,3-trifluoro-2-(trifluoromethyl)propanoyl fluoride in an aqueous phase and remove the same. This enables the fluoromethane to be selectively obtained.

In the above process, an alcohol may be used instead of water or an aqueous alkaline solution. Inexpensive alcohols are preferable in terms of cost. Examples of usable alcohols include methanol, ethanol, propanol, and the like. Of these, methanol is particularly preferable. Bringing the product into contact with an alcohol to produce an ester makes combustion treatment easier.

With respect to the method for selectively obtaining 3,3,3-trifluoro-2-(trifluoromethyl)propanoyl fluoride from the pyrolyzed product, the product obtained by pyrolysis may be directly subjected to a distillation operation to remove fluoromethane as a column top component. Thus, the 3,3,3-trifluoro-2-(trifluoromethyl)propanoyl fluoride can be obtained as a column bottom component.

Advantageous Effects of Invention

According to the method of the present invention, the desired fluoromethane and 3,3,3-trifluoro-2-(trifluoromethyl)propanoyl fluoride can be obtained with high conversion of the starting material and high selectivity by a simple process in which a pyrolysis reaction is performed in a gas phase, using 1,1,3,3,3-pentafluoro-2-trifluoromethylpropyl methyl ether, an inexpensive material, as a starting material without using a catalyst that is difficult to handle.

The fluoromethane ($CH_3F$) obtained by the method of the present invention is useful as an etching gas for forming a state-of-the-art microstructure in a semiconductor process, and the 3,3,3-trifluoro-2-(trifluoromethyl)propanoyl fluoride obtained by the method of the present invention is useful as an alternative gas that is a replacement for etching gases or cleaning gases, such as $NF_3$, $SF_6$, and $C_2F_6$, which are used in large quantities in the production processes of semiconductors and liquid crystals and have large global warming effects.

Therefore, the method of the present invention is industrially highly useful as a method for producing these compounds efficiently, inexpensively, and safely.

DESCRIPTION OF EMBODIMENTS

Hereinafter, the present invention is described in more detail with reference to Examples.

Examples 1 to 5

γ-alumina ($Al_2O_3$) A (pore volume of 0.45 ml/g) (average particle size of 3 mm) that was not fluorinated was used as a catalyst. The catalyst was placed in a tubular Hastelloy reactor with an inner diameter of 15 mm and a length of 650 mm. The reactor was heated to 200° C., and 1,1,3,3,3-pentafluoro-2-trifluoromethylpropyl methyl ether, which is a starting material, was supplied to the reactor. Table 1 shows the contact time: W/F (g·sec/cc), i.e., the ratio of the amount of the catalyst W (g) relative to the supply rate F (cc/sec) of the starting material.

The outlet gas from the reaction tube was analyzed using gas chromatography. Table 1 shows the analysis results. The numerical values shown in Table 1 are the component proportions (mol %) determined by multiplying the area ratio of each peak obtained by the gas chromatography by a coefficient for correcting a sensitivity to each gas.

The terms described in Table 1 represent the following compounds.
$CH_3F$: fluoromethane
$C_3H_6$: propene
HFC-1225zc: $CF_2$=$CHCF_3$
HFC-236fa: $CF_3CH_2CF_3$
OIME: 1,1,3,3,3-pentafluoro-2-trifluoromethylpropyl methyl ether
Fluoride: 3,3,3-trifluoro-2-(trifluoromethyl)propanoyl fluoride

TABLE 1

| Ex. | Contact Time W/F | Conversion (%) | Analysis results (%) | | | | | | | Yield of CH$_3$F (%) | Yield of Fluoride (%) |
|---|---|---|---|---|---|---|---|---|---|---|---|
| | | | CH$_3$F | C$_3$H$_6$ | HFC-1225zc | HFC-236fa | OIME | Fluoride | Others | | |
| 1 | 1  | 95.2 | 50.0 | 0.03 | 0    | 0.05 | 2.4 | 45.7 | 1.8 | 99 | 91 |
| 2 | 3  | 99.6 | 48.8 | 0    | 0.7  | 0.03 | 0.2 | 49.9 | 0.4 | 98 | 99 |
| 3 | 5  | 100  | 47.9 | 0.05 | 0.4  | 0.08 | 0   | 51.3 | 1.6 | 97 | 99 |
| 4 | 10 | 100  | 49.7 | 0.03 | 0.6  | 0.05 | 0   | 49.5 | 0.1 | 99 | 99 |
| 5 | 15 | 96.6 | 48.7 | 0    | 1.1  | 0.15 | 1.7 | 48.4 | 0   | 97 | 97 |

The low-boiling-point component containing CH$_3$F and the high-boiling-point component containing fluoride were separately analyzed. The analysis results in Table 1 show the ratio, expressed as a percentage, of each of them to all of the components.

As is clear from the above results, the two desired compounds, i.e., fluoromethane (CH$_3$F) and 3,3,3-trifluoro-2-(trifluoromethyl)propanoyl fluoride ((CF$_3$)$_2$CHCOF), can be obtained as main components by a pyrolysis reaction of 1,1,3,3,3-pentafluoro-2-trifluoromethylpropyl methyl ether. The yields of these compounds were both 91% or more, and impurities were suppressed to 0.8% to 2.1%.

Example 6

The gas obtained after the pyrolysis in Example 4 was passed through a 5 wt % KOH aqueous solution, so that CH$_3$F accounted for 99.5% of the gas component. This result confirms that 3,3,3-trifluoro-2-(trifluoromethyl)propanoyl fluoride can be separated and removed by bringing the produced gas after pyrolysis into contact with an aqueous alkaline solution. Further, the gas obtained after the separation was cooled, collected, and subjected to rectification, thereby obtaining CH$_3$F with a purity of 99.99%.

Example 7

Under the same conditions as those of Examples 1 to 5, the reactor was heated to 150° C., and 1,1,3,3,3-pentafluoro-2-trifluoromethylpropyl methyl ether, which is a starting material, was supplied to the reactor.

Example 8

Under the same conditions as those of Examples 1 to 5, the reactor was heated to 250° C., and 1,1,3,3,3-pentafluoro-2-trifluoromethylpropyl methyl ether, which is a starting material, was supplied to the reactor.

Table 2 below shows the results obtained by analyzing the outlet gas from the reactor using gas chromatography.

TABLE 2

| Ex. | Contact Time W/F | Conversion (%) | Analysis results (%) | | | | | | | Yield of CH$_3$F (%) | Yield of Fluoride (%) |
|---|---|---|---|---|---|---|---|---|---|---|---|
| | | | CH$_3$F | C$_3$H$_6$ | HFC-1225zc | HFC-236fa | OIME | Fluoride | Others | | |
| 7 | 10 | 99.8 | 46.5 | 0   | 1.32 | 0.05 | 0.1 | 50   | 2.0 | 93 | 100 |
| 8 | 10 | 96   | 48   | 0.4 | 0.8  | 0.3  | 1.9 | 45.1 | 3.5 | 92 | 87  |

As is clear from the above results, when the temperature of the pyrolysis was 150° C. (Example 7), the conversion was nearly 100%, and the yield of the product was high. When the temperature of the pyrolysis was 250° C. (Example 8), the conversion slightly decreased, but the yield of CH$_3$F was maintained at a high value of 92%.

Examples 9 to 11

α-alumina (Example 9), TiO$_2$ (Example 10), or CrO$_2$ (Example 11) was used as a catalyst. Under the same conditions as those of Examples 1 to 5, the reactor was heated to 150° C., and 1,1,3,3,3-pentafluoro-2-trifluoromethylpropyl methyl ether, which is a starting material, was supplied to the reactor.

TABLE 3

| Ex. | Contact Time W/F | Conversion (%) | Selectivity (%) | | | | | | Yield of CH$_3$F (%) | Yield of Fluoride (%) |
|---|---|---|---|---|---|---|---|---|---|---|
| | | | CH$_3$F | C$_3$H$_6$ | HFC-1225zc | HFC-236fa | Fluoride | Others | | |
| 9  | 5 | 77  | 49.7 | 0 | 0.1 | 0 | 49.6 | 0.6 | 77 | 76  |
| 10 | 5 | 100 | 49.4 | 0 | 0   | 0 | 50   | 0.6 | 99 | 100 |
| 11 | 5 | 74  | 49.3 | 0 | 0.1 | 0 | 49.7 | 0.9 | 73 | 74  |

The selectivity in Table 3 shows the proportions, expressed in percentages, of the reaction product excluding unreacted OIME.

When α-alumina (Example 9) or $CrO_2$ (Example 11) was used, the conversion decreased, but the selectivity of $CH_3F$ and fluoride was high. Since the selectivity is high, $CH_3F$ and fluoride can be obtained with high yields if the unreacted starting material is returned to the reactor.

Examples 12 to 17

Under the same conditions as those of Examples 1 to 5, the reactor was heated to 200° C. 1,1,3,3,3-pentafluoro-2-trifluoromethylpropyl methyl ether in an amount of 15 cc/min, which is a starting material, was mixed with nitrogen in an amount of 15 cc/min, and the mixture was supplied to the reactor. A catalyst that was not fluorinated and had a different pore volume, i.e., γ-alumina ($Al_2O_3$) B (pore volume of 0.38 ml/g), C (pore volume of 0.43 ml/g), or D (pore volume of 0.64 ml/g) was used. γ-alumina B, C, and D had an average particle size of 3 mm. Table 4 shows the results of Example 12 obtained when a reaction was performed using B, the results of Example 13 obtained when a reaction was performed using C, and the results of Example 14 obtained when a reaction was performed using D. When C and D, which had larger pore volumes, were used, the yields of $CH_3F$ and fluoride were 99%.

Further, these reactions were continuously carried out for 100 hours. The results of Example 15 were obtained using B in the reaction for 100 hours, the results of Example 16 were obtained using C in the reaction for 100 hours, and the results of Example 17 were obtained using D in the reaction for 100 hours.

As shown in Examples 15 to 17, the larger the pore volume, the smaller the decrease in the conversion and selectivity regarding $CH_3F$ and fluoride, and the longer the catalyst can be used even without regeneration.

TABLE 4

| Ex. | Contact Time W/F | Conversion (%) | Selectivity (%) | | | | | Yield of $CH_3F$ (%) | Yield of Fluoride (%) |
| --- | --- | --- | --- | --- | --- | --- | --- | --- | --- |
| | | | $CH_3F$ | $C_3H_6$ | HFC-1225zc | HFC-236fa | Fluoride | Others | | |
| 12 | 5 | 96.0 | 49.8 | 0 | 0.2 | 0 | 49.6 | 0.4 | 96 | 95 |
| 13 | 5 | 99.8 | 49.9 | 0 | 0.1 | 0 | 49.9 | 0.1 | 99 | 99 |
| 14 | 5 | 99.9 | 49.8 | 0 | 0.1 | 0 | 49.9 | 0.1 | 99 | 99 |
| 15 | 5 | 54 | 48.1 | 0 | 0.5 | 0 | 47.7 | 3.7 | 52 | 52 |
| 16 | 5 | 73 | 49.9 | 0 | 0.1 | 0 | 49.9 | 0.1 | 73 | 73 |
| 17 | 5 | 90 | 49.7 | 0 | 0 | 0 | 49.7 | 0.6 | 89 | 89 |

Examples 18 to 20

Under the same conditions as those of Examples 1 to 5, the reactor was heated to 150° C., and 1,1,3,3,3-pentafluoro-2-trifluoromethylpropyl methyl ether, which is a starting material, was supplied to the reactor. As a catalyst, γ-alumina ($Al_2O_3$) D (pore volume of 0.64 ml/g) (average particle size of 3 mm) that was not fluorinated was used.

The results of Example 18 were obtained when a reaction was continuously carried out for 370 hours. The conversion regarding $CH_3F$ and fluoride decreased, but the selectivity remained high. The results of Example 19 were obtained when a reaction was performed in the same manner as in Example 17 except that W/F was changed from 5 (g·sec/cc) to 10 (g·sec/cc). The conversion was restored by increasing W/F, showing 98%.

Then, the catalyst was removed, and composition analysis of the surface thereof was performed by XPS (ESCA). The composition of the outermost surface was as follows: 25 wt % of fluorine, 8 wt % of carbon, 26 wt % of oxygen, and 41 wt % of aluminum.

The results of Example 20 were obtained when a reaction was continuously carried out at W/F=30 (g·sec/cc) for 700 hours. The conversion and selectivity regarding $CH_3F$ and fluoride remained high. When W/F was increased and 1,1,3,3,3-pentafluoro-2-trifluoromethylpropyl methyl ether was sufficiently contacted with the catalyst, the conversion and selectivity were high even if the reaction was performed for a long period of time.

TABLE 5

| Ex. | Contact Time W/F | Conversion (%) | Selectivity (%) | | | | | | Yield of CH$_3$F (%) | Yield of Fluoride (%) |
| --- | --- | --- | --- | --- | --- | --- | --- | --- | --- | --- |
| | | | CH$_3$F | C$_3$H$_6$ | HFC-1225zc | HFC-236fa | Fluoride | Others | | |
| 18 | 5 | 59 | 49.8 | 0 | 0.1 | 0 | 49.3 | 0.8 | 59 | 58 |
| 19 | 10 | 98.0 | 48.8 | 0 | 1.1 | 0.1 | 49.9 | 0.1 | 96 | 98 |
| 20 | 30 | 96.7 | 49.8 | 0 | 0 | 0 | 49.9 | 0.3 | 96 | 97 |

Examples 21 and 22

Under the same conditions as those of Examples 1 to 5, the reactor was heated to 150° C., and 1,1,3,3,3-pentafluoro-2-trifluoromethylpropyl methyl ether, which is a starting material, was supplied to the reactor.

As a catalyst, silica alumina A (SiO$_2$/Al$_2$O$_3$=68 wt %/26 wt %) or silica alumina A (SiO$_2$/Al$_2$O$_3$=83 wt %/13 wt %) was used. The conversion and selectivity regarding CH$_3$F and fluoride were high.

Example 23

3.6 g of γ-alumina (Al$_2$O$_3$) D (pore volume of 0.64 ml/g) (average particle size of 3 mm) that was not fluorinated was placed in a tubular Hastelloy reactor with an inner diameter of 15 mm and a length of 650 mm. The reactor was heated to 350° C. while nitrogen was supplied in an amount of 50 cc/min. Trifluoromethane was then supplied thereto in an amount of 50 cc/min, and the mixed gas of nitrogen and trifluoromethane was allowed to flow at a trifluoromethane concentration of 50 vol % for 30 minutes to fluorinate the γ-alumina. Composition analysis of the surface of the catalyst was performed by XPS (ESCA). The composition of the outermost surface was as follows: 25 wt % of fluorine, 5 wt % of carbon, 29 wt % of oxygen, and 41 wt % of aluminum. Using the thus-obtained fluorinated γ-alumina catalyst, the reactor was heated to 150° C., and 1,1,3,3,3-pentafluoro-2-trifluoromethylpropyl methyl ether, which is a starting material, was supplied to the reactor.

The conversion was 100%, and the yield of CH$_3$F and the yield of fluoride were 96% and 100%, respectively.

TABLE 6

| Ex. | Contact Time W/F | Conversion (%) | Selectivity (%) | | | | | | Yield of CH$_3$F (%) | Yield of Fluoride (%) |
| --- | --- | --- | --- | --- | --- | --- | --- | --- | --- | --- |
| | | | CH$_3$F | C$_3$H$_6$ | HFC-1225zc | HFC-236fa | Fluoride | Others | | |
| 21 | 5 | 100 | 49.3 | 0 | 0.6 | 0 | 49.9 | 0.1 | 98 | 99 |
| 22 | 5 | 97.1 | 49.8 | 0 | 0.2 | 0 | 47.3 | 0.1 | 99 | 94 |
| 23 | 2 | 100 | 48.1 | 0 | 1.4 | 0.1 | 50 | 0.4 | 96 | 100 |

The invention claimed is:

1. A method for producing fluoromethane and 3,3,3-trifluoro-2-(trifluoromethyl)propanoyl fluoride, the method comprising pyrolyzing 1,1,3,3,3-pentafluoro-2-trifluoromethylpropyl methyl ether in a gas phase in the presence of a γ-alumina catalyst and/or silica alumina catalyst.

2. The method according to claim 1, wherein the 1,1,3,3,3-pentafluoro-2-trifluoromethylpropyl methyl ether used as a starting material is obtained by reacting perfluoroisobutylene and methanol.

3. The method according to claim 1, comprising the steps of:
(1) reacting perfluoroisobutylene and methanol to obtain 1,1,3,3,3-pentafluoro-2-trifluoromethylpropyl methyl ether; and
(2) pyrolyzing the 1,1,3,3,3-pentafluoro-2-trifluoromethylpropyl methyl ether obtained in step (1) in a gas phase in the presence of a catalyst to obtain fluoromethane and 3,3,3-trifluoro-2-(trifluoromethyl)propanoyl fluoride.

4. The method according to claim 1, wherein the catalyst has a pore volume of 0.5 ml/g or more.

5. The method according to claim 1, wherein the reaction temperature of the pyrolysis reaction is in the range of 100 to 400° C.

6. The method according to claim 1, wherein the pressure during the pyrolysis reaction is in the range of 0.05 to 1 MPa.

7. The method according to claim 1, further comprising, after obtaining the pyrolyzed product comprising fluoromethane and 3,3,3-trifluoro-2-(trifluoromethyl)propanoyl fluoride, the step of cooling the product to separate it into a low-boiling-point component comprising the fluoromethane and a high-boiling-point component comprising the 3,3,3-trifluoro-2-(trifluoromethyl)propanoyl fluoride.

8. The method according to claim 1, further comprising, after obtaining the pyrolyzed product comprising fluoromethane and 3,3,3-trifluoro-2-(trifluoromethyl)propanoyl fluoride, the step of bringing the product into contact with water or an aqueous alkaline solution to remove the 3,3,3-trifluoro-2-(trifluoromethyl)propanoyl fluoride.

9. The method according to claim 1, further comprising, after obtaining the pyrolyzed product comprising fluoromethane and 3,3,3-trifluoro-2-(trifluoromethyl)propanoyl fluoride, the step of subjecting the product to a distillation operation to obtain the 3,3,3-trifluoro-2-(trifluoromethyl)propanoyl fluoride as a column bottom component.

10. The method according to claim 1, further comprising, after obtaining the pyrolyzed product comprising fluoromethane and 3,3,3-trifluoro-2-(trifluoromethyl)propanoyl fluoride, the step of bringing the product into contact with an alcohol to remove the 3,3,3-trifluoro-2-(trifluoromethyl)propanoyl fluoride.

11. The method according to claim 10, wherein the alcohol is at least one member selected from the group consisting of methanol, ethanol, and propanol.

\* \* \* \* \*